US009265822B2

(12) United States Patent
Hoft

(10) Patent No.: US 9,265,822 B2
(45) Date of Patent: Feb. 23, 2016

(54) PEPTIDES FOR INDUCING HETEROSUBTYPIC INFLUENZA T CELL RESPONSES

(75) Inventor: Daniel Hoft, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 447 days.

(21) Appl. No.: 12/895,289

(22) Filed: Sep. 30, 2010

(65) Prior Publication Data

US 2011/0076297 A1 Mar. 31, 2011

Related U.S. Application Data

(60) Provisional application No. 61/247,038, filed on Sep. 30, 2009.

(51) Int. Cl.

| | |
|---|---|
| *A61K 39/00* | (2006.01) |
| *A61K 38/08* | (2006.01) |
| *A61K 38/10* | (2006.01) |
| *A61K 39/145* | (2006.01) |
| *C07K 7/06* | (2006.01) |
| *C07K 14/005* | (2006.01) |
| *A61K 39/12* | (2006.01) |
| *A61K 38/00* | (2006.01) |

(52) U.S. Cl.

CPC ............... *A61K 39/145* (2013.01); *A61K 39/12* (2013.01); *C07K 7/06* (2013.01); *C07K 14/005* (2013.01); *A61K 38/00* (2013.01); *A61K 2039/545* (2013.01); *A61K 2039/55* (2013.01); *C12N 2760/16122* (2013.01); *C12N 2760/16134* (2013.01)

(58) Field of Classification Search

None

See application file for complete search history.

(56) References Cited

U.S. PATENT DOCUMENTS

| | | | | |
|---|---|---|---|---|
| 5,591,430 | A * | 1/1997 | Townsend et al. | 424/93.71 |
| 2002/0032162 | A1 | 3/2002 | Content et al. | 514/44 R |
| 2002/0147167 | A1 | 10/2002 | Armstrong et al. | 514/44 R |
| 2008/0032921 | A1 * | 2/2008 | Alexander et al. | 514/2 |
| 2010/0068224 | A1 * | 3/2010 | Crea et al. | 424/202.1 |

FOREIGN PATENT DOCUMENTS

| | | | |
|---|---|---|---|
| WO | WO 96/10631 | * | 4/1996 |
| WO | WO 99/45954 | * | 9/1999 |
| WO | WO 2006-124408 | | 11/2006 |
| WO | WO 2008/039267 | * | 4/2008 |
| WO | WO 2008-044032 | | 4/2008 |

OTHER PUBLICATIONS

PCT International Search Report and Written Opinion issued in International Application No. PCT/US10/50836, dated Feb. 11, 2011.

PCT Invitation to Pay Additional Fees issued in International Application No. PCT/US10/50836, dated Nov. 22, 2010.

Extended European Search Report issued on Jun. 6, 2013 for European Patent Application No. EP 10 82 1219.

Heiny, et al., "Evolutionarily Conserved Protein Sequences of Influenza A Viruses, Avian and Human, as Vaccine Targets," PLoS One, 2(11):e1190, 2007.

Office Action issued in Japanese Application No. 2012-532299, mailed Sep. 17, 2014.

* cited by examiner

*Primary Examiner* — Shanon A Foley

*Assistant Examiner* — Myron Hill

(74) *Attorney, Agent, or Firm* — Parker Highlander PLLC

(57) ABSTRACT

The present invention provides compositions and methods for generation of an anti-influenza immune response. In particular, conserved T cell epitopes within matrix protein and nucleoprotein components of influenza virus have been identified and further screened for those structures that will bind either or both of HLA I and II molecules. Methods for vaccinating subjects with formulations of such peptides for the treatment or prevention of influenza infaction also are described.

15 Claims, 2 Drawing Sheets

SEQUENCE LISTING

```
<160> NUMBER OF SEQ ID NOS: 51

<210> SEQ ID NO 1
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 1

Asn Met Asp Arg Ala Val Lys Leu Tyr
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Asn Thr Asp Leu Glu Ala Leu Met Glu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Gly Ile Leu Gly Phe Val Phe Thr Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Ile Leu Ser Pro Leu Thr Lys Gly Ile
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Val Leu Ala Ser Thr Thr Ala Lys Ala
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Ala Leu Ala Ser Cys Met Gly Leu Ile
1               5

<210> SEQ ID NO 7
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 7

Ile Leu Gly Phe Val Phe Thr Leu Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Arg Leu Glu Asp Val Phe Ala Gly Lys
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Arg Pro Ile Leu Ser Pro Leu Thr Lys
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Val Phe Ala Gly Lys Asn Thr Asp Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Asp Pro Asn Asn Met Asp Arg Ala Val
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Ala Leu Ser Tyr Ser Thr Gly Ala Leu
1               5

<210> SEQ ID NO 13
<211> LENGTH: 9
<212> TYPE: PRT
<213> ORGANISM: Artificial Sequence
<220> FEATURE:
```

```
<223> OTHER INFORMATION: Synthetic peptide

<400> SEQUENCE: 13

Trp Leu Lys Thr Arg Pro Ile Leu Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Met Glu Trp Leu Lys Thr Arg Pro Ile
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Ala Glu Ile Ala Gln Arg Leu Glu Asp
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Val Pro Glu Ser Met Arg Glu Glu Tyr
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17

Ser Ser Asp Pro Leu Val Val Ala Ala
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide

<400> SEQUENCE: 18

Val Val Ala Ala Ser Ile Ile Gly Ile
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 19

Lys Arg Gly Pro Ser Thr Glu Gly Val
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

Pro Leu Val Val Ala Ala Ser Ile Ile
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Gly Leu Lys Arg Gly Pro Ser Thr Glu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide

<400> SEQUENCE: 22

Asp Pro Leu Val Val Ala Ala Ser Ile
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide

<400> SEQUENCE: 23

Gly Pro Ser Thr Glu Gly Val Pro Glu
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide

<400> SEQUENCE: 24

Ala Ser Gln Gly Thr Lys Arg Ser Tyr
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 25

Ala Thr Glu Ile Arg Ala Ser Val Gly
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide

<400> SEQUENCE: 26

Gly Met Asp Pro Arg Met Cys Ser Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Ser Ala Leu Ile Leu Arg Gly Ser Val
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Ile Leu Lys Gly Lys Phe Gln Thr Ala
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide

<400> SEQUENCE: 29

Ile Leu Arg Gly Ser Val Ala His Lys
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic peptide

<400> SEQUENCE: 30

Ala Leu Ile Leu Arg Gly Ser Val Ala
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide

<400> SEQUENCE: 31
```

Asp Pro Lys Lys Thr Gly Gly Pro Ile
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide

<400> SEQUENCE: 32

Asn Pro Ile Val Pro Ser Phe Asp Met
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide

<400> SEQUENCE: 33

Glu Leu Arg Ser Arg Tyr Trp Ala Ile
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide

<400> SEQUENCE: 34

Glu Glu Ile Arg Arg Ile Trp Arg Gln
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic peptide

<400> SEQUENCE: 35

Ala Thr Tyr Gln Arg Thr Arg Ala Leu
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide

<400> SEQUENCE: 36

Ala Arg Gln Met Val Gln Ala Met Arg
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic peptide

<400> SEQUENCE: 37

```
Ala Tyr Gln Lys Arg Met Gly Val Gln
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide

<400> SEQUENCE: 38

Leu Lys Ala Glu Ile Ala Gln Arg Leu
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Phe Val Phe Thr Leu Thr Val Pro Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide

<400> SEQUENCE: 40

Arg Arg Phe Val Gln Asn Ala Leu Asn
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide

<400> SEQUENCE: 41

Asn Pro Leu Ile Arg His Glu Asn Arg
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42

Leu Val Val Ala Ala Ser Ile Ile Gly
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide

<400> SEQUENCE: 43

Ile Arg Pro Asn Glu Asn Pro Ala His
```

```
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide

<400> SEQUENCE: 44

Phe Tyr Ile Gln Met Cys Thr Glu Leu
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide

<400> SEQUENCE: 45

Tyr Trp Ala Ile Arg Thr Arg Ser Gly
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide

<400> SEQUENCE: 46

Trp Ala Ile Arg Thr Arg Ser Gly Gly
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic peptide

<400> SEQUENCE: 47

Ser Tyr Phe Phe Gly Asp Asn Ala Glu
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48

Ser Leu Ile Arg Pro Asn Glu Asn Pro
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide

<400> SEQUENCE: 49

Thr Tyr Gln Arg Thr Arg Ala Leu Val
1               5
```

```
<210> SEQ ID NO 50
<211> LENGTH: 9
<212> TYPE: PRT
<213> ORGANISM: Artificial Sequence
<220> FEATURE:
<223> OTHER INFORMATION: Synthetic peptide

<400> SEQUENCE: 50

Tyr Gln Arg Thr Arg Ala Leu Val Arg
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide

<400> SEQUENCE: 51

Arg Arg Ile Trp Arg Gln Ala Asn Asn
1               5
```

US 9,265,822 B2

PEPTIDES FOR INDUCING HETEROSUBTYPIC INFLUENZA T CELL RESPONSES

This application claims benefit of priority to U.S. Provisional Application Ser. No. 61/247,038, filed Sep. 30, 2009, the entire contents of which are hereby incorporated by reference.

BACKGROUND OF THE INVENTION

1. Field of the Invention

The present invention relates generally to the fields of virology and immunotherapy. More particularly, it concerns the identification of immunostimulatory peptides and the development of peptide vaccines for the treatment and prevention of influenza.

2. Description of Related Art

Influenza, commonly referred to as the flu, is an infectious disease caused by RNA viruses of the family Orthomyxoviridae (the influenza viruses), that affects birds and mammals. The most common symptoms of the disease are chills, fever, pharyngitis, muscle pains, severe headache, coughing, weakness and general discomfort. Fever and coughs are the most frequent symptoms. In more serious cases, influenza causes pneumonia, which can be fatal, particularly for the young and the elderly. Although it is often confused with the common cold, influenza is a much more severe disease and is caused by a different type of virus. Influenza may produce nausea and vomiting, particularly in children, but these symptoms are more common in the unrelated disease gastroenteritis, which is sometimes called "stomach flu" or "24-hour flu."

Typically, influenza is transmitted from infected mammals through the air by coughs or sneezes, creating aerosols containing the virus, and from infected birds through their droppings. Influenza can also be transmitted by saliva, nasal secretions, feces and blood. Infections also occur through contact with these body fluids or with contaminated surfaces. Flu viruses can remain infectious for about one week at human body temperature, over 30 days at 0° C. (32° F.), and for much longer periods at very low temperatures. Influenza viruses can be inactivated by disinfectants and detergents. As the virus can be inactivated by soap, frequent hand washing reduces the risk of infection.

Flu spreads around the world in seasonal epidemics, resulting in the deaths of hundreds of thousands annually—millions in pandemic years. Three influenza pandemics occurred in the 20th century and killed tens of millions of people, with each of these pandemics being caused by the appearance of a new strain of the virus in humans. Often, these new strains result from the spread of an existing flu virus to humans from other animal species. An avian strain named H5N1 has recently posed the greatest risk for a new influenza pandemic since it first killed humans in Asia in the 1990's.

Vaccinations against influenza are usually given to people in developed countries and to farmed poultry. The most common human vaccine is the trivalent influenza vaccine (TIV) that contains purified and inactivated material from three viral strains. Typically, this vaccine includes material from two influenza A virus subtypes and one influenza B virus strain. The TIV carries no risk of transmitting the disease, and it has very low reactivity. A vaccine formulated for one year may be ineffective in the following year, since the influenza virus evolves rapidly, and different strains become dominant. Antiviral drugs can be used to treat influenza, with neuraminidase inhibitors being particularly effective.

The symptoms of human influenza were first described nearly 2,400 years ago. Since then, the virus has caused numerous pandemics. Historical data on influenza are difficult to interpret, because the symptoms can be similar to those of other diseases, such as diphtheria, pneumonic plague, typhoid fever, dengue, or typhus. The first convincing record of an influenza pandemic was of an outbreak in 1580, which began in Russia and spread to Europe via Africa. In Rome, over 8,000 people were killed, and several Spanish cities were almost wiped out. Pandemics continued sporadically throughout the 17th and 18th centuries, with the pandemic of 1830-1833 being particularly widespread; it infected approximately a quarter of the people exposed. The most famous and lethal outbreak was the so-called Spanish flu pandemic (type A influenza, H1N1 subtype), which lasted from 1918 to 1919. It is not known exactly how many it killed, but estimates range from 20 to 100 million people. Later flu pandemics were not so devastating. They included the 1957 Asian Flu (type A, H2N2 strain) and the 1968 Hong Kong Flu (type A, H3N2 strain), but even these smaller outbreaks killed millions of people. In later pandemics, antibiotics were available to control secondary infections and this may have helped reduce mortality compared to the Spanish Flu of 1918.

In April 2009, a novel H1N1 flu strain that combined genes from human, pig, and bird flu, initially dubbed the "swine flu," emerged in Mexico, the United States, and several other nations. By late April, the H1N1 swine flu was suspected of having killed over 150 in Mexico, and prompted concern that a new pandemic was imminent. The structural similarity to the 1918 Spanish Flu, possibly the greatest medical disaster of all times, highlights to ongoing threat from influenza virus generally, and the H1N1 subtype in particular. Therefore, compositions and methods for the prevention and treatment of this disease remain highly sought after.

SUMMARY OF THE INVENTION

Thus, in accordance with the present invention, there is provided a peptide comprising an amino acid sequence selected from the group consisting of SEQ ID NO:1-51. The peptide may be about 9-15 residues in length, about 9-13 residues in length, or about 9-11 residues in length, including 9, 10, 11, 12, and 13 residues. The peptide may be fused to another amino acid sequence. The peptide may be formulated in a pharmaceutically acceptable buffer, diluent or excipient, or may be lyophilized, and optionally may be formulated with an adjuvant.

In another embodiment, there is provided a method of inducing an immune response in a subject comprising administering to a subject one or more peptides comprising an amino acid sequence selected from the group consisting of SEQ ID NO:1-51. The peptide or peptides may be about 9-15 residues in length, about 9-13 residues in length, or about 9-11 residues in length, including 9, 10, 11, 12, and 13 residues. The peptide or peptides may be fused to another amino acid sequence.

The method may comprise administering at least 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, or all 51 peptides to the subject. The method may comprise administering at least one peptide binding Class I HLA and at least one peptide binding Class II HLA to the subject. The method may comprise administering at least one peptide from a matrix protein and at least one peptide from a nucleoprotein, or at least one peptide from a matrix 1 protein, at least one peptide from a matrix 2 protein, and at least one peptide from a nucleoprotein. Further, the method may comprise administering a sufficient number of peptides to the subject to target 100% of HLA haplotypes in a population.

Administration may comprise injection, such as subcutaneous or intramuscular injection. Administration may comprise inhalation, such as administering a intanasal aerosol or mist. The peptide or peptides may be administered with an adjuvant, such as a squalene adjuvant, a cytokine adjuvant, a lipid adjuvant or a TLR ligand. The total amount of peptide administered may be between 50 µg/kg and 1 mg/kg. The peptide or peptides may be administered at least a second time, and the second administration may comprise at least one peptide distinct from the peptide or peptides of the initial administration. The method may further comprise administration of a live-attenuated vaccine or a killed vaccine to said subject. The subject may be a human subject or a non-human animal subject. The method may further comprise measuring a $CD4^+$, a $CD8^+$ and/or a γδ T cell response in the subject following administration.

In yet another embodiment, there is provided a vaccine formulation comprising one or more peptides comprising an amino acid sequence selected from the group consisting of SEQ ID NO:1-51. The peptide or peptides may be 9-15 residues in length. The peptide or peptides may be fused to another amino acid sequence. The formulation may comprise an adjuvant. The formulation may be an injectable formulation or an inhalable formulation. The formulation may be provided in a unit dosage of between 50 µg/kg and 1 mg/kg. The formulation may be lyophilized or in a liquid form, such as in a pharmaceutically acceptable buffer, carrier or diluent, and may also include an adjuvant.

The formulation may comprise at least 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, or all 51 peptides. The formulation may comprise at least one peptide binding Class I HLA and at least one peptide binding Class II HLA. The formulation may comprise at least one peptide from a matrix protein and at least one peptide from a nucleoprotein, or at least one peptide from a matrix 1 protein, at least one peptide from a matrix 2 protein, and at least one peptide from a nucleoprotein. The formulation may comprise a sufficient number of distinct peptides to target 100% of HLA haplotypes.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
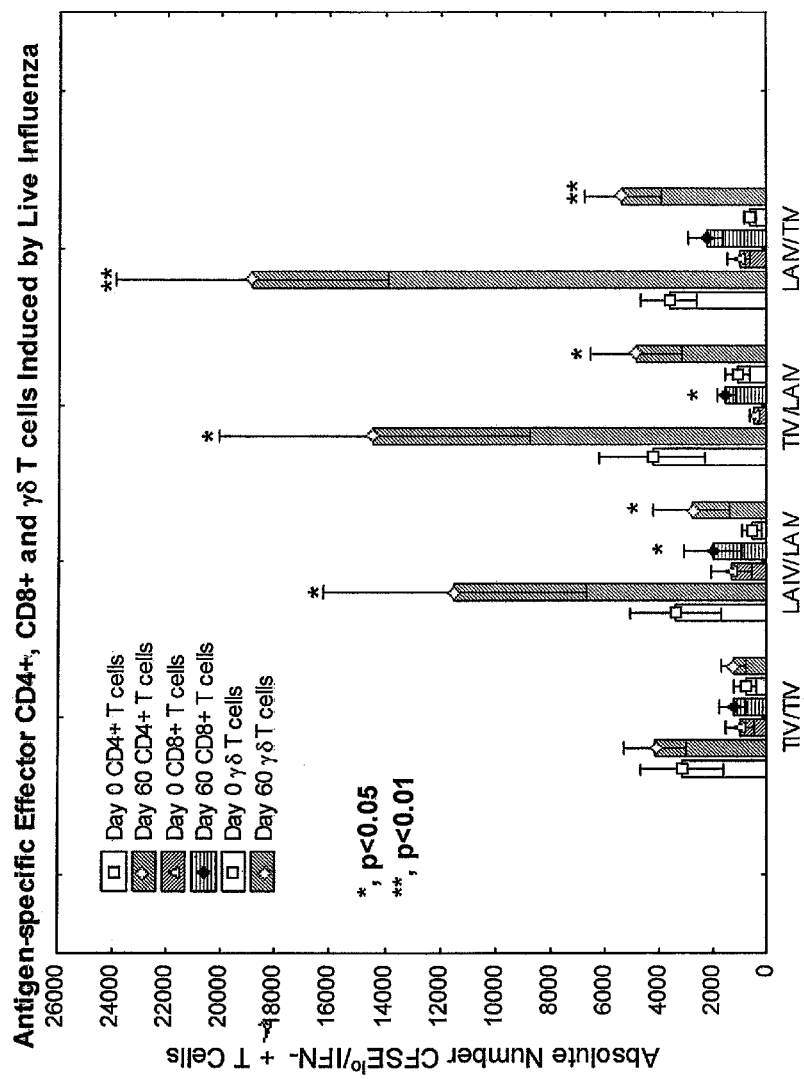
FIG. 1—Overall CFSE Results. n=10-13/group.

As discussed above, influenza virus is the leading viral cause of severe respiratory tract illness in person of all age, and can also cause severe illness and death in the very young and elderly. Some particularly lethal strains can be fatal to even healthy young adults. All of these patient groups would benefit from more effective anti-viral therapeutic options for influenza virus, and in particular, the H1N1 subtype responsible for the 1918 and 2009 influenza outbreaks.

The present invention provides new vaccine compositions that can be delivered in the same manner as currently approved vaccines. The identified peptide components target conserved epitopes that have a high probability of stimulating protective T cell responses, and when used together in multi-peptide formulations, can do so in the entire population. These and other aspects of the invention are described in detail below.

I. DEFINITIONS

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment.

An "epitope," also known as an antigenic determinant, is the part of a macromolecule that is recognized by the immune system, specifically by antibodies, B cells, or T cells.

"Major histocompatibility complex" or "MHC" is a cluster of genes that plays a role in control of the cellular interactions responsible for physiologic immune responses. In humans, the MHC complex is also known as the HLA complex. For a detailed description of the MHC and HLA complexes (see Paul, 1993).

"Human leukocyte antigen" or "HLA" is a human class I or class II major histocompatibility complex (MHC) protein (see, e.g., Stites, 1994).

An "HLA supertype or family," as used herein, describes sets of HLA molecules grouped on the basis of shared peptide-binding specificities. HLA class I molecules that share somewhat similar binding affinity for peptides bearing certain amino acid motifs are grouped into HLA supertypes. The terms HLA superfamily, HLA supertype family, HLA family, and HLA xx-like supertype molecules (where xx denotes a particular HLA type), are synonyms.

The term "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs are typically different for each protein encoded by each human HLA allele and differ in the pattern of the primary and secondary anchor residues.

A "supermotif" is a peptide binding specificity shared by HLA molecules encoded by two or more HLA alleles. Thus, a preferably is recognized with high or intermediate affinity (as defined herein) by two or more HLA antigens.

"Cross-reactive binding" indicates that a peptide is bound by more than one HLA molecule; a synonym is degenerate binding.

A "protective immune response" refers to a T cell response to an antigen derived from an infectious agent, which prevents or at least partially arrests disease symptoms or infection. The immune response may also include an antibody response which has been facilitated by the stimulation of helper T cells.

II. INFLUENZA VIRUS

A. General

The etiological cause of influenza, the Orthomyxoviridae family of viruses, was first discovered in pigs by Richard Shope in 1931. This discovery was shortly followed by the isolation of the virus from humans by a group headed by Patrick Laidlaw at the Medical Research Council of the United Kingdom in 1933. However, it was not until Wendell Stanley first crystallized tobacco mosaic virus in 1935 that the non-cellular nature of viruses was appreciated.

The first significant step towards preventing influenza was the development in 1944 of a killed-virus vaccine for influenza by Thomas Francis, Jr. This built on work by Australian Frank Macfarlane Burnet, who showed that the virus lost virulence when it was cultured in fertilized hen's eggs. Application of this observation by Francis allowed his group of researchers at the University of Michigan to develop the first influenza vaccine, with support from the U.S. Army. The Army was deeply involved in this research due to its experience of influenza in World War I, when thousands of troops were killed by the virus in a matter of months.

Although there were scares in the State of New Jersey in 1976 (with the Swine Flu), worldwide in 1977 (with the Russian Flu), and in Hong Kong and other Asian countries in 1997 (with H5N1 avian influenza), there have been no major pandemics since the 1968 Hong Kong Flu. Immunity to previous pandemic influenza strains and vaccination may have limited the spread of the virus and may have helped prevent further pandemics.

The influenza virus is an RNA virus of the family Orthomyxoviridae, which comprises five genera: Influenzavirus A, Influenzavirus B, Influenzavirus C, Isavirus and Thogotovirus. The Influenzavirus A genus has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses. The serotypes that have been confirmed in humans, ordered by the number of known human pandemic deaths, are:

H1N1, which caused Spanish flu in 1918 and has been identified as the serotype of the 2009 outbreak of swine flu originating from Mexico
H2N2, which caused Asian Flu in 1957
H3N2, which caused Hong Kong Flu in 1968
H5N1, a pandemic threat in the 2007-08 flu season
H7N7, which has unusual zoonotic potential
H1N2, endemic in humans and pigs
H9N2
H7N2
H7N3
H10N7

Influenza viruses bind to cells through sialic acid sugars on the surfaces of epithelial cells; typically in the nose, throat and lungs of mammals and intestines of birds. The cell imports the virus by endocytosis. In the acidic endosome, part of the viral hemagglutinin protein fuses the viral envelope with the vacuole's membrane, releasing the viral RNA (vRNA) molecules, accessory proteins and RNA-dependent RNA polymerase into the cytoplasm. These proteins and vRNA form a complex that is transported into the cell nucleus, where the RNA-dependent RNA polymerase begins transcribing complementary positive-sense vRNA. The vRNA is either exported into the cytoplasm and translated, or remains in the nucleus. Newly-synthesised viral proteins are either secreted through the Golgi apparatus onto the cell surface or transported back into the nucleus to bind vRNA and form new viral genome particles. Other viral proteins have multiple actions in the host cell, including degrading cellular mRNA and using the released nucleotides for vRNA synthesis and also inhibiting translation of host-cell mRNAs.

Negative-sense vRNAs that form the genomes of future viruses, RNA-dependent RNA polymerase, and other viral proteins are assembled into a virion. Hemagglutinin and neuraminidase molecules cluster into a bulge in the cell membrane. The vRNA and viral core proteins leave the nucleus and enter this membrane protrusion. The mature virus buds off from the cell in a sphere of host phospholipid membrane, acquiring hemagglutinin and neuraminidase with this membrane coat. As before, the viruses adhere to the cell through hemagglutinin; the mature viruses detach once their neuraminidase has cleaved sialic acid residues from the host cell. After the release of new influenza viruses, the host cell dies.

Because of the absence of RNA proofreading enzymes, the RNA-dependent RNA polymerase makes a single nucleotide insertion error roughly every 10 thousand nucleotides, which is the approximate length of the influenza vRNA. Hence, the majority of newly-manufactured influenza viruses are mutants, causing "antigenic drift." The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

B. The 1918 "Spanish" Flu

The 1918 flu pandemic, commonly referred to as the Spanish Flu, was an influenza pandemic that spread to nearly every part of the world. It was caused by an unusually virulent and deadly Influenza A virus strain of subtype H1N1. Historical and epidemiological data are inadequate to identify the geographic origin of the virus. Most of its victims were healthy young adults, in contrast to most influenza outbreaks which predominantly affect juvenile, elderly, or otherwise weakened patients. The pandemic lasted from March 1918 to June 1920, spreading even to the Arctic and remote Pacific islands. It is estimated that anywhere from 20 to 100 million people were killed worldwide, or the approximate equivalent of one third of the population of Europe, more than double the number killed in World War I. This extraordinary toll resulted from the extremely high illness rate of up to 50% and the extreme severity of the symptoms, suspected to be caused by cytokine storms. The pandemic is estimated to have affected up to one billion people—half the world's population at the time.

Scientists have used tissue samples from frozen victims to reproduce the virus for study. Among the conclusions of this research is that the virus kills via a cytokine storm, an overreaction of the body's immune system, which explains its unusually severe nature and the concentrated age profile of its victims. The strong immune systems of young adults ravaged the body, whereas the weaker immune systems of children and middle-aged adults caused fewer deaths.

The global mortality rate from the 1918/1919 pandemic is not known, but is estimated at 2.5 to 5% of those who were infected died. Note this does not mean that 2.5-5% of the human population died; with 20% or more of the world population suffering from the disease to some extent, a case-fatality ratio this high would mean that about 0.5-1% ($\approx$50 million) of the whole population died. Influenza may have killed as many as 25 million in its first 25 weeks. Older estimates say it killed 40-50 million people while current estimates say 50 million to 100 million people worldwide were killed. This pandemic has been described as "the greatest medical holocaust in history" and may have killed more people than the Black Death.

As many as 17 million died in India, about 5% of India's population at the time. In Japan, 23 million persons were affected, and 390,000 died. In the U.S., about 28% of the population suffered, and 500,000 to 675,000 died. In Britain as many as 250,000 died; in France more than 400,000. In Canada approximately 50,000 died. Entire villages perished in Alaska and southern Africa. Estimates for the fatalities in the capital city, Addis Ababa, range from 5,000 to 10,000, with some experts opining that the number was even higher, while in British Somaliland one official there estimated that 7% of the native population died from influenza. In Australia an estimated 12,000 people died and in the Fiji Islands, 14% of the population died during only two weeks, and in Western Samoa 22%.

This huge death toll was caused by an extremely high infection rate of up to 50% and the extreme severity of the symptoms, suspected to be caused by cytokine storms. Indeed, symptoms in 1918 were so unusual that initially influenza was misdiagnosed as dengue, cholera, or typhoid. One observer wrote, "One of the most striking of the complications was hemorrhage from mucous membranes, especially from the nose, stomach, and intestine. Bleeding from the ears and petechial hemorrhages in the skin also occurred." The majority of deaths were from bacterial pneumonia, a secondary infection caused by influenza, but the virus also killed people directly, causing massive hemorrhages and edema in the lung.

The unusually severe disease killed between 2 and 20% of those infected, as opposed to the more usual flu epidemic mortality rate of 0.1%. Another unusual feature of this pandemic was that it mostly killed young adults, with 99% of pandemic influenza deaths occurring in people under 65, and more than half in young adults 20 to 40 years old. This is unusual since influenza is normally most deadly to the very young (under age 2) and the very old (over age 70), and may have been due to partial protection caused by exposure to a previous Russian flu pandemic of 1889. Another oddity was that this influenza outbreak was widespread in summer and fall (in the Northern Hemisphere). Typically, influenza is worse in the winter months.

People without symptoms could be stricken suddenly and within hours be too weak to walk; many died the next day. Symptoms included a blue tint to the face and coughing up blood caused by severe obstruction of the lungs. In some cases, the virus caused an uncontrollable hemorrhaging that filled the lungs, and patients drowned in their body fluids (pneumonia). In others, the flu caused frequent loss of bowel control and the victim would die from losing critical intestinal lining and blood loss.

In fast-progressing cases, mortality was primarily from pneumonia, by virus-induced consolidation. Slower-progressing cases featured secondary bacterial pneumonias, and there may have been neural involvement that led to mental disorders in a minority of cases. Some deaths resulted from malnourishment and even animal attacks in overwhelmed communities.

One theory is that the virus strain originated at Fort Riley, Kans., by two genetic mechanisms—genetic drift and antigenic shift—in viruses in poultry and swine which the fort bred for food; the soldiers were then sent from Fort Riley to different places around the world, where they spread the disease. However, evidence from a recent reconstruction of the virus suggests that it jumped directly from birds to humans, without traveling through swine.

An effort to recreate the 1918 flu strain (a subtype of avian strain H1N1) was a collaboration among the Armed Forces Institute of Pathology, Southeast Poultry Research Laboratory and Mount Sinai School of Medicine in New York; the effort resulted in the announcement (on Oct. 5, 2005) that the group had successfully determined the virus's genetic sequence, using historic tissue samples recovered by pathologist Johan Hultin from a female flu victim buried in the Alaskan permafrost and samples preserved from American soldiers.

Kobasa et al. (2007) reported that monkeys (*Macaca fascicularis*) infected with the recreated strain exhibited classic symptoms of the 1918 pandemic and died from a cytokine storm—an overreaction of the immune system. This may explain why the 1918 flu had its surprising effect on younger, healthier people, as a person with a stronger immune system would potentially have a stronger overreaction. In December, 2008 research by Yoshihiro Kawaoka of University of Wisconsin linked the presence of three specific genes (termed PA, PB1, and PB2) and a nucleoprotein derived from 1918 flu samples to the ability of the flu virus to invade the lungs and cause pneumonia. The combination triggered similar symptoms in animal testing.

C. The 2009 "Swine" Flu

The 2009 swine flu outbreak is an epidemic that began in April 2009 with a new strain of influenza virus. The new strain is commonly called swine flu, but some parties object to the name and it has also been referred to as Mexican flu, swine-origin influenza, North American influenza, and 2009 H1N1 flu. On Apr. 30, 2009, the World Health Organization called it influenza A(H1N1). The outbreak is believed to have started in March 2009. Local outbreaks of an influenza-like illness were first detected in three areas of Mexico, but the virus responsible was not clinically identified as a new strain until Apr. 24, 2009. Following the identification, its presence was soon confirmed in various Mexican states and in Mexico City. Within days, isolated cases (and suspected cases) were identified elsewhere in Mexico, the U.S., and several other Northern Hemisphere countries.

By Apr. 28, 2009, the new strain was confirmed to have spread to Spain, the United Kingdom, New Zealand, and Israel, and the virus was suspected in many other nations, with a total of over 3,000 candidate cases, prompting the World Health Organization (WHO) to change its pandemic alert phase to "Phase 5," which denotes "widespread human infection." Despite the scale of the alert, the WHO stated on Apr. 29, 2009 that the majority of people infected with the virus have made a full recovery without need of medical attention or anti-viral drugs. The common human H1N1 influenza virus affects millions of people every year according to the WHO, causing 250,000 and 500,000 deaths every year around the world. In industrialized countries, most of these deaths occur in those 65 or older.

In March and April 2009, over 3000 cases of suspected swine flu in humans were detected in Mexico and the southwestern United States. The disease was detected in several countries on multiple continents within weeks of its initial discovery. The strain appears to be unusually lethal in Mexico but not in other countries. There have also been cases reported in the states of San Luis Potosí, Hidalgo, Querétaro and Mexico State. The Mexican fatalities are mainly young adults of 25 to 45, a common trait of pandemic flu.

The CDC has confirmed that U.S. cases were found to be made up of genetic elements from four different flu viruses—North American swine influenza, North American avian influenza, human influenza, and swine influenza virus typically found in Asia and Europe—"an unusually mongrelised mix of genetic sequences." Pigs have been shown to act as a potential "mixing vessel" in which reassortment can occur between flu viruses of several species. This new strain appears to be a result of the reassortment of two swine influenza viruses, which themselves are descended from previous reassortments in pigs. Influenza viruses readily undergo reassortment because their genome is split between eight pieces of RNA (see Orthomyxoviridae). The virus was resistant to amantadine and rimantadine, but susceptible to oseltamivir (Tamiflu®) and zanamivir (Relenza®).

Gene sequences for every viral gene were made available through the Global Initiative on Sharing Avian Influenza Data (GISAID). Preliminary genetic characterization found that the hemagglutinin (HA) gene was similar to that of swine flu viruses present in U.S. pigs since 1999, but the neuraminidase (NA) and matrix protein (M) genes resembled versions present in European swine flu isolates. The six genes from American swine flu are themselves mixtures of swine flu, bird flu, and human flu viruses. While viruses with this genetic makeup had not previously been found to be circulating in humans or pigs, there is no formal national surveillance system to determine what viruses are circulating in pigs in the U.S. The seasonal influenza strain H1N1 vaccine is thought to be unlikely to provide protection.

The CDC has not fully explained why the U.S. cases were primarily mild disease while the Mexican cases had led to multiple deaths. However, research on previous pandemic strains has suggested that mortality can vary widely between different countries, with mortality being concentrated in the developing world. Differences in the viruses or co-infection are also being considered as possible causes. Of the fourteen initial samples from Mexico tested by the CDC, seven were found to match the American strain. The virus likely passes through several cycles of infection with no known linkages between patients in Texas and California, and that containment of the virus is "not very likely."

D. Diagnosis

Symptoms of influenza can start quite suddenly one to two days after infection. Usually the first symptoms are chills or a chilly sensation, but fever is also common early in the infection, with body temperatures ranging from 38-39° C. (approximately 100-103° F.). Many people are so ill that they are confined to bed for several days, with aches and pains throughout their bodies, which are worse in their backs and legs. Symptoms of influenza may include:

Body aches, especially joints and throat
Extreme coldness and fever
Fatigue
Headache
Irritated watering eyes
Reddened eyes, skin (especially face), mouth, throat and nose
Abdominal pain (in children with influenza B)

It can be difficult to distinguish between the common cold and influenza in the early stages of these infections, but a flu can be identified by a high fever with a sudden onset and extreme fatigue. Diarrhea is not normally a symptom of influenza in adults, although it has been seen in some human cases of the H5N1 "bird flu" and can be a symptom in children.

Since anti-viral drugs are effective in treating influenza if given early, it can be important to identify cases early. Of the symptoms listed above, the combinations of fever with cough, sore throat and/or nasal conjection can improve diagnostic accuracy. Two decision analysis studies suggest that during local outbreaks of influenza, the prevalence will be over 70%, and thus patients with any of these combinations of symptoms may be treated with neuramidase inhibitors without testing. Even in the absence of a local outbreak, treatment may be justified in the elderly during the influenza season as long as the prevalence is over 15%.

The available laboratory tests for influenza continue to improve. The United States Centers for Disease Control and Prevention (CDC) maintains an up-to-date summary of available laboratory tests. According to the CDC, rapid diagnostic tests have a sensitivity of 70-75% and specificity of 90-95% when compared with viral culture. These tests may be especially useful during the influenza season (prevalence=25%) but in the absence of a local outbreak, or peri-influenza season (prevalence=10%).

Influenza's effects are much more severe and last longer than those of the common cold. Most people will recover in about one to two weeks, but others will develop life-threatening complications (such as pneumonia). Influenza, however, can be deadly, especially for the weak, old or chronically ill. The flu can worsen chronic health problems. People with emphysema, chronic bronchitis or asthma may experience shortness of breath while they have the flu, and influenza may cause worsening of coronary heart disease or congestive heart failure. Smoking is another risk factor associated with more serious disease and increased mortality from influenza.

Common symptoms of the flu such as fever, headaches, and fatigue come from the huge amounts of proinflammatory cytokines and chemokines (such as interferon or tumor necrosis factor) produced from influenza-infected cells. In contrast to the rhinovirus that causes the common cold, influenza does cause tissue damage, so symptoms are not entirely due to the inflammatory response. This massive immune response can produce a life-threatening cytokine storm. This effect has been proposed to be the cause of the unusual lethality of both the H5N1 avian influenza, and the 1918 pandemic strain (see above).

In some cases, an autoimmune response to an influenza infection may contribute to the development of Guillain-Barré syndrome. However, as many other infections can increase the risk of this disease, influenza may only be an important cause during epidemics. This syndrome can also be a rare side-effect of influenza vaccines, with an incidence of about one case per million vaccinations.

People with the flu are advised to get plenty of rest, drink plenty of liquids, avoid using alcohol and tobacco and, if necessary, take medications such as paracetamol (acetaminophen) to relieve the fever and muscle aches associated with the flu. Children and teenagers with flu symptoms (particularly fever) should avoid taking aspirin during an influenza infection (especially influenza type B), because doing so can lead to Reye's syndrome, a rare but potentially fatal disease of the liver. Since influenza is caused by a virus, antibiotics have no effect on the infection; unless prescribed for secondary infections such as bacterial pneumonia, they may lead to resistant bacteria. Anti-viral medication can be effective, but some strains of influenza can show resistance to the standard anti-viral drugs (see below).

III. INFLUENZA PEPTIDES

A. Influenza Virus Structural Proteins

As discussed above, the three major genera of influenza virus are Influenzavirus A, B and C. Influenzavirus A has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses.

Influenzavirus B has one species, influenza B virus. Influenza B almost exclusively infects humans and is less common than influenza A. The only other animals known to be susceptible to influenza B infection are the seal and the ferret. This type of influenza mutates at a rate 2-3 times lower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

Influenzavirus C has one species, influenza C virus, which infects humans, dogs and pigs, sometimes causing both severe illness and local epidemics. However, influenza C is less common than the other types and usually only causes mild disease in children.

Influenzaviruses A, B and C are very similar in overall structure. The virus particle is 80-120 nanometers in diameter and usually roughly spherical, although filamentous forms can occur. These filamentous forms are more common in influenza C, which can form cordlike structures up to 500 micrometers long on the surfaces of infected cells. However, despite these varied shapes, the viral particles of all influenza viruses are similar in composition. These are made of a viral envelope containing two main types of glycoproteins, wrapped around a central core. The central core contains the viral RNA genome and other viral proteins that package and protect this RNA.

Unusually for a virus, its genome is not a single piece of nucleic acid; instead, it contains seven or eight pieces of segmented negative-sense RNA, each piece of RNA contains either one or two genes. For example, the influenza A genome contains 11 genes on eight pieces of RNA, encoding for 11 proteins: hemagglutinin (HA), neuraminidase (NA), nucleoprotein (NP), M1, M2, NS1, NS2(NEP), PA, PB1, PB1-F2 and PB2.

Hemagglutinin (HA) and neuraminidase (NA) are the two large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins are targets for anti-viral drugs. Furthermore, they are antigens to which antibodies can be raised. Influenza A viruses are classified into subtypes based on antibody responses to HA and NA. These different types of HA and NA form the basis of the H and N distinctions in, for example, H5N1. There are 16 H and 9 N subtypes known, but only H1, H2 and H3, and N1 and N2 are commonly found in humans.

B. Peptide Compositions

As used herein, an "antigenic composition" comprises an influenza virus peptide antigen. Of particular interest here are peptides from the M1, M2 and NP molecules, and conserved epitopes therein. In particular embodiments, the antigenic composition comprises or encodes one or more peptides comprising one or more sequences shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:50, and SEQ ID NO:51, or an immunologically functional equivalent thereof. These sequences are shown in tabular form below in Tables 1-2.

TABLE 1

Conserved HLA class I binding epitopes from M1, M2 and NP*

| Influenza proteins | HLA class I | Prevalence of HLA subtypes (%) | | | Starting Position | Amino Acid Sequence 1 2 3 4 5 6 7 8 9 | SEQ ID NO |
|---|---|---|---|---|---|---|---|
| | | White | Black | Hisp | | | |
| M1 | HLA-A*01 | 14.07 | 4.85 | 3.66 | 92 | N M̲ D R A V K̲ L Y | 1 |
| M1 | | | | | 36 | N T̲ D L E A L̲ M E | 2 |
| M1 | HLA-A*0201 | 45.8 | 30.3 | 54 | 58 | G I L G F V̲ F T L | 3 |
| M1 | | | | | 51 | I L S P L T̲ K G I | 4 |
| M1 | | | | | 181 | V L A S T T̲ A K A | 5 |
| M1 | | | | | 124 | A L A S C M̲ G L I | 6 |
| M1 | | | | | 59 | I L G F V F̲ T L T | 7 |

TABLE 1-continued

Conserved HLA class I binding epitopes from M1, M2 and NP*

| Influenza proteins | HLA class I | Prevalence of HLA subtypes (%) | | | Amino Acid Starting Position | Sequence 1 2 3 4 5 6 7 8 9 | SEQ ID NO |
|---|---|---|---|---|---|---|---|
| | | White | Black | Hisp | | | |
| M1 | HLA-A*03 | 11.9 | 6.48 | 3.26 | 27 | R L E D V F A G K | 8 |
| M1 | | | | | 49 | R P I L S P L T K | 9 |
| M1 | HLA-A*2402 | 16.8 | 8.8 | 26.7 | 31 | V F A G K N T D L | 10 |
| M1 | | | | | 58 | G I L G F V F T L | 3 |
| M1 | HLA-B*0702 | 17.7 | 15.5 | 11.8 | 89 | D P N N M D R A V | 11 |
| M1 | | | | | 117 | A L S Y S T G A L | 12 |
| M1 | HLA-B*08 | 18.1 | 6.3 | 9 | 45 | W L K T R P I L S | 13 |
| M1 | | | | | 31 | V F A G K N T D L | 10 |
| M1 | HLA-B*4402 | 19.7 | 10.5 | 17.4 | 43 | M E W L K T R P I | 14 |
| M1 | | | | | 22 | A E I A Q R L E D | 15 |
| M2 | HLA-A*01 | 14.07 | 4.85 | 3.66 | 68 | V P E S M R E E Y | 16 |
| M2 | | | | | 22 | S S D P L V V A A | 17 |
| M2 | HLA-A*0201 | 45.8 | 30.3 | 54 | 27 | V V A A S I I G I | 18 |
| M2 | | | | | 22 | S S D P L V V A A | 17 |
| M2 | | | | | 60 | K R G P S T E G V | 19 |
| M2 | | | | | 25 | P L V V A A S I I | 20 |
| M2 | | | | | 58 | G L K R G P S T E | 21 |
| M2 | HLA-A*03 | 11.9 | 6.48 | 3.26 | 58 | G L K R G P S T E | 21 |
| M2 | | | | | 25 | P L V V A A S I I | 20 |
| M2 | HLA-A*2402 | 16.8 | 8.8 | 26.7 | 24 | D P L V V A A S I | 22 |
| M2 | | | | | 27 | V V A A S I I G I | 18 |
| M2 | HLA-B*0702 | 17.7 | 15.5 | 11.8 | 24 | D P L V V A A S I | 22 |
| M2 | | | | | 62 | G P S T E G V P E | 23 |
| M2 | HLA-B*08 | 18.1 | 6.3 | 9 | 58 | G L K R G P S T E | 21 |
| M2 | | | | | 24 | D P L V V A A S I | 22 |
| M2 | HLA-B*4402 | 19.7 | 10.5 | 17.4 | 27 | V V A A S I I G I | 18 |
| M2 | | | | | 24 | D P L V V A A S I | 22 |
| NP | HLA-A*01 | 14.1 | 4.85 | 3.66 | 2 | A S Q G T K R S Y | 24 |
| NP | | | | | 22 | A T E I R A S V G | 25 |
| NP | HLA-A*0201 | 45.8 | 30.3 | 54 | 158 | G M D P R M C S L | 26 |
| NP | | | | | 262 | S A L I L R G S V | 27 |
| NP | | | | | 225 | I L K G K F Q T A | 28 |
| NP | | | | | 265 | I L R G S V A H K | 29 |
| NP | HLA-A*03 | 11.9 | 6.48 | 3.26 | 265 | I L R G S V A H K | 29 |
| NP | | | | | 263 | A L I L R G S V A | 30 |
| NP | HLA-B*0702 | 17.7 | 15.5 | 11.8 | 88 | D P K K T G G P I | 31 |

TABLE 1-continued

Conserved HLA class I binding epitopes from M1, M2 and NP*

| Influenza proteins | HLA class I | Prevalence of HLA subtypes (%) | | | Starting Position | Amino Acid Sequence 1 2 3 4 5 6 7 8 9 | SEQ ID NO |
|---|---|---|---|---|---|---|---|
| | | White | Black | Hisp | | | |
| NP | | | | | 473 | N P I V P S F D M | 32 |
| NP | HLA-B*08 | 18.1 | 6.3 | 9 | 380 | E L R S R Y W A I | 33 |
| NP | | | | | 225 | I L K G K F Q T A | 28 |
| NP | HLA-B*4402 | 19.7 | 10.5 | 17.4 | 114 | E E I R R I W R Q | 34 |
| NP | | | | | 146 | A T Y Q R T R A L | 35 |

*Total number of peptides in this pool is 35 (13 peptides predicted to bind to multiple HLA subtypes).

TABLE 2

Conserved HLA class II binding epitopes from M1, M2 and NP proteins*

| Influenza proteins | HLA class II | HLA Subtype Prevalence (%) | | | Starting Position | Amino Acid Sequence | SEQ ID NO |
|---|---|---|---|---|---|---|---|
| | | white | Black | Hisp. | | | |
| M1 | HLA_DQ7oDQB1s0301 c.p.mtx | 28.5 | 23.1 | 48 | 209 | ARQMVQAMR | 36 |
| M1 | HLA_DR1.p.mtx | 18.5 | 8.4 | 10.1 | 239 | AYQKRMGVQ | 37 |
| M1 | HLA_DR1oDRB1s0101 c.p.mtx | 18.5 | 8.4 | 10.1 | 20 | LKAEIAQRL | 38 |
| M1 | HLA_DR3.p.mtx | 17.7 | 19.5 | 14.4 | 20 | LKAEIAQRL | 38 |
| M1 | HLA_DR4.p.mtx | 23.6 | 6.1 | 29.8 | 62 | FVFTLTVPS | 39 |
| M1 | HLA_DR7.p.mtx | 26.2 | 11.1 | 16.6 | 77 | RRFVQNALN | 40 |
| M1 | HLA_DR8oDRB1s0801 c.p.mtx | 5.5 | 10.9 | 23.3 | 170 | NPLIRHENR | 41 |
| M2 | HLA_DR4oDRB1s0401 c.p.mtx | 23.6 | 6.1 | 29.8 | 26 | LVVAASIIG | 42 |
| NP | HLA_DQ7oDQB1s0301 c.p.mtx | 28.1 | 23.1 | 48 | 376 | IRPNENPAH | 43 |
| NP | HLA_DR1.p.mtx | 18.5 | 8.4 | 10.1 | 99 | FYIQMCTEL | 44 |
| NP | HLA_DR11oDRB1s1101 c.p.m | 17 | 18 | 18 | 445 | YWAIRTRSG | 45 |
| NP | HLA_DR14.p.mtx | 2.4 | 3.8 | 15.2 | 446 | WAIRTRSGG | 46 |
| NP | HLA_DR15oDRB1s1501 c.p.mtx | 19.9 | 14.8 | 15 | 546 | SYFFGDNAE | 47 |
| NP | HLA_DR1oDRB1s0101 c.p.mtx | 18.5 | 8.4 | 10.1 | 445 | YWAIRTRSG | 45 |
| NP | HLA_DR3.p.mtx | 17.7 | 19.5 | 14.4 | 374 | SLIRPNENP | 48 |
| NP | HLA_DR4oDRB1s0401 c.p.mtx | 23.6 | 6.1 | 29.8 | 445 | YWAIRTRSG | 45 |
| NP | HLA_DR7.p.mtx | 26.2 | 11.1 | 16.6 | 207 | TYQRTRALV | 49 |
| NP | HLA_DR7oDRB1s0701 c.p.mtx | 26.2 | 11.1 | 16.6 | 208 | YQRTRALVR | 50 |
| NP | HLA_DR8oDRB1s0801 c.p.mtx | 5.5 | 10.9 | 23.3 | 177 | RRIWRQANN | 51 |

*Total number of peptides in this pool is 16 (3 peptides predicted to bind to multiple HLA subtypes).

As used herein, an "amino acid" or "amino acid residue" refers to any naturally-occurring amino acid, any amino acid derivative or any amino acid mimic known in the art, including modified or unusual amino acids. In certain embodiments, the natural residues of the peptide are sequential, without any non-amino acid interrupting the sequence of natural amino acid residues. In other embodiments, the sequence may comprise one or more non-natural amino acid moieties.

The peptides of the present invention can be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), Houghten et al. (1985). In some embodiments, peptide synthesis is contemplated by using automated peptide synthesis machines, such as those available from Applied Biosystems (Foster City, Calif.). The peptides of the present invention may be isolated and extensively dialyzed to remove undesired small molecular weight molecules and/or lyophilized for more ready formulation into a desired vehicle.

The term "peptide" is used interchangeably with "oligopeptide" in the present specification to designate a series of residues, typically L-amino acids, connected one to the other, typically by peptide bonds between the α-amino and carboxyl groups of adjacent amino acids. Particular T cell-inducing oligopeptides of the invention are 15 residues or less in length and usually consist of between about 8 and about 13 residues, particularly 9 to 11 residues. Specific lengths of 9, 10, 11, 12, 13, 14 and 15 residues are contemplated.

An "immunogenic peptide" or "peptide epitope" is a peptide which comprises an allele-specific motif or supermotif such that the peptide will bind an HLA molecule and induce a T cell response. Thus, immunogenic peptides of the invention are capable of binding to an appropriate HLA molecule and thereafter inducing a T cell response to the antigen from which the immunogenic peptide is derived.

Modified or unusual amino acid include, but are not limited to, those shown on Table 3 below.

TABLE 3

Modified and Unusual Amino Acids

| Abbr. | Amino Acid |
|---|---|
| Aad | 2-Aminoadipic acid |
| Baad | 3-Aminoadipic acid |
| Bala | 2-alanine, -Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| Ahyl | Allo-Hydroxylysine |
| 3Hyp | 3-Hydroxyproline |
| 4Hyp | 4-Hydroxyproline |
| Ide | Isodesmosine |
| Aile | Allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In particular embodiments, biocompatible protein, polypeptide or peptide containing compositions will generally be mammalian proteins or peptides or synthetic proteins or peptides each essentially free from toxins, pathogens and harmful immunogens.

C. Variants

The present invention also contemplates modification of the peptides shown in Tables 1 and 2. Such peptide "variants" may include additional residues, such as additional N- or C-terminal amino acids, or altered/substituted/modified amino acids, and yet still comprise one of the sequences disclosed herein, so long as the sequence meets the criteria set forth above, including the maintenance of biological activity.

The following is a discussion based upon changing the amino acids of a peptide to create a variant peptide. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

A specialized kind of insertional variant is the fusion protein. This molecule generally has all or a substantial portion of the native molecule, linked at the N- or C-terminus, to all or a portion of a second peptide or polypeptide. In particular, embodiments where multiple peptides of the present invention (SEQ ID NOS:1-51) are linked in a "head-to-tail" fashion to create a polytope molecule, i.e., an epitope multimer. The peptides may be linked to each directly though peptide bonds, or they may be separated by peptide "spacers," or they may be attached using non-peptide or peptoid "linker," which are well known in the art. In addition, inclusion of a cleavage site at or near the fusion junction or linker will facilitate removal or release of other peptide sequences. Other useful fusions include linking of functional domains, such as active sites from enzymes such as a hydrolase, glycosylation domains, cellular targeting signals or transmembrane regions.

D. Peptide Purification

In certain embodiments the peptides of the present invention may be purified. The term "purified peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein/peptide purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying a tumor-associated HLA-restricted peptide of the present invention, it may be desirable to express the polypeptide in a prokaryotic or eukaryotic expression system and extract the protein using denaturing conditions. The polypeptide may be purified from other cellular components using an affinity column, which binds to a tagged portion of the polypeptide. Although this preparation will be purified in an inactive form, the denatured material will still be capable of transducing cells. Once inside of the target cell or tissue, it is generally accepted that the polypeptide will regain full biological activity.

As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

IV. VACCINE PROTOCOLS AND FORMULATIONS

In an embodiment of the present invention, a method of treatment and prevention of influenza by the delivery of a peptide or peptide composition is contemplated. An effective amount of the vaccine composition, generally, is defined as that amount sufficient to detectably and repeatedly ameliorate, reduce, minimize or limit the extent of the disease or condition or symptoms thereof. More rigorous definitions may apply, including elimination, eradication or cure of disease.

A. Administration

The peptides of the present invention may be used in vivo to produce anti-influenza virus immune response, and thus constitute therapeutic and prophylactic vaccines. Thus, the peptides can be formulated for parenteral administration, e.g., formulated for injection via the intradermal, intravenous, intramuscular, subcutaneous, or intraperitoneal routes. Administration by the intradermal and intramuscular routes are specifically contemplated. The vaccine can also be administered by a topical route directly to the mucosa, for example by nasal drops or mist, inhalation, or by nebulizer.

Some variation in dosage and regimen will necessarily occur depending on the age and medical condition of the subject being treated, as well as the route chosen. The person responsible for administration will, in any event, determine the appropriate dose for the individual subject. In many instances, it will be desirable to have multiple administrations of the vaccine. Thus, the compositions of the invention may be administered 1, 2, 3, 4, 5, 6, 7, 8, 9, 10, or more times. The administrations will normally be at from one to twelve week intervals, more usually from one to six week intervals. Periodic re-administration will be desirable with recurrent exposure to the pathogen.

The administration may use various "unit doses." Unit dose is defined as containing a predetermined-quantity of the therapeutic composition. The quantity to be administered, and the particular route and formulation, are within the skill of those in the clinical arts.

B. Measuring Immune Responses

One of ordinary skill would know various assays to determine whether an immune response against a peptide was generated. The phrase "immune response" includes both cellular and humoral immune responses. Various B lymphocyte and T lymphocyte assays are well known, such as ELISAs, cytotoxic T lymphocyte (CTL) assays, such as chromium release assays, proliferation assays using peripheral blood lymphocytes (PBL), tetramer assays, and cytokine production assays. See Benjamini et al. (1991), hereby incorporated by reference.

C. Injectable Formulations

One method for the delivery of a pharmaceutical according to the present invention is via injection. However, the pharmaceutical compositions disclosed herein may alternatively be administered intravenously, intradermally, intramuscularly, or even intraperitoneally as described in U.S. Pat. No.

5,543,158; U.S. Pat. No. 5,641,515 and U.S. Pat. No. 5,399,363 (each specifically incorporated herein by reference in its entirety).

Injection may be by syringe or any other method used for injection of a solution, as long as the agent can pass through the particular gauge of needle required for injection. A novel needleless injection system has been described (U.S. Pat. No. 5,846,233) having a nozzle defining an ampule chamber for holding the solution and an energy device for pushing the solution out of the nozzle to the site of delivery.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. Sterile aqueous media that can be employed will be known to those of skill in the art in light of the present disclosure. For example, one dosage may be dissolved in 1 ml of isotonic NaCl solution and either added to 1000 ml of hypodermolysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous injectable composition that contains a protein as an active ingredient is well understood in the art.

D. Inhalable or Aerosol Formulations

A particular mode of administration contemplated by the inventor for the peptides of the present invention is via inhalation and/or administration to the nasal mucosa, i.e., intranasal administration. A variety of commercial vaccines (influenza, measles) are currently administered using a nasal mist formulation. The methods of the present invention can be carried out using a delivery similar to that used with the Flu-Mist® product, which employs the BD AccuSpray® System (Becton Dickinson). Also useful for this route are nebulizers, such as jet nebulizers and ultrasonic nebulizers.

E. Additional Vaccine Components

In other embodiments of the invention, the antigenic composition may comprise an additional immunostimulatory agent. Immunostimulatory agents include but are not limited to an additional antigens, an immunomodulator, an antigen presenting cell or an adjuvant. In other embodiments, one or more of the additional agent(s) is covalently bonded to the antigen or an immunostimulatory agent, in any combination.

i. Adjuvants

As also well known in the art, the immunogenicity of a particular immunogen composition can be enhanced by the use of non-specific stimulators of the immune response, known as adjuvants. Adjuvants have been used experimentally to promote a generalized increase in immunity against unknown antigens (e.g., U.S. Pat. No. 4,877,611). Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. Suitable molecule adjuvants include all acceptable immunostimulatory compounds, such as cytokines, toxins or synthetic compositions.

Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant. Other adjuvants that may also be used include IL-1, IL-2, IL-4, IL-7, IL-12, γ-interferon, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MHC antigens may even be used.

In one aspect, an adjuvant effect is achieved by use of an agent, such as alum, used in about 0.05 to about 0.1% solution in phosphate buffered saline. Alternatively, the antigen is made as an admixture with synthetic polymers of sugars (Carbopol®) used as an about 0.25% solution. Adjuvant effect may also be made my aggregation of the antigen in the vaccine by heat treatment with temperatures ranging between about 70° to about 101° C. for a 30 second to 2-minute period, respectively. Aggregation by reactivating with pepsin-treated (Fab) antibodies to albumin, mixture with bacterial cell(s) such as *C. parvum*, an endotoxin or a lipopolysaccharide component of Gram-negative bacteria, emulsion in physiologically acceptable oil vehicles, such as mannide mono-oleate (Aracel A), or emulsion with a 20% solution of a perfluorocarbon (Fluosol-DA®) used as a block substitute, also may be employed.

Some adjuvants, for example, certain organic molecules obtained from bacteria, act on the host rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

In certain embodiments, hemocyanins and hemoerythrins may also be used in the invention. The use of hemocyanin from keyhole limpet (KLH) is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin.

Another group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is described for use in artificial liposomes formed from phosphatidyl choline and phosphatidyl glycerol. It is the to be effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present invention.

BCG (*bacillus* Calmette-Guerin, an attenuated strain of *Mycobacterium*) and BCG-cell wall skeleton (CWS) may also be used as adjuvants, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945. BCG is an important clinical tool because of its immunostimulatory properties. BCG acts to stimulate the reticulo-endothelial system, activates natural killer cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990). Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Lotte et al., 1984). It is one of the few vaccines that can be given at birth, it engenders long-lived immune responses with only a single dose, and there is a worldwide distribution network with experience in BCG vaccination. An exemplary BCG vaccine is sold as TICE BCG (Organon Inc., West Orange, N.J.).

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., 1994) may also be employed. Oligonucleotides are another useful group of adjuvants (Yamamoto et al., 1988). Quil A and lentinen are other adjuvants that may be used in certain embodiments of the present invention.

Another group of adjuvants are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

Those of skill in the art will know the different kinds of adjuvants that can be conjugated to cellular vaccines in accordance with this invention and these include alkyl lysophosphilipids (ALP); BCG; and biotin (including biotinylated derivatives) among others. Certain adjuvants particularly contemplated for use are the teichoic acids from Gram-cells. These include the lipoteichoic acids (LTA), ribitol teichoic acids (RTA) and glycerol teichoic acid (GTA). Active forms of their synthetic counterparts may also be employed in connection with the invention (Takada et al., 1995).

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

Adjuvants may be encoded by a nucleic acid (e.g., DNA or RNA). It is contemplated that such adjuvants may be also be encoded in a nucleic acid (e.g., an expression vector) encoding the antigen, or in a separate vector or other construct. Nucleic acids encoding the adjuvants can be delivered directly, such as for example with lipids or liposomes.

ii. Biological Response Modifiers

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m$^2$) (Johnson/Mead, NJ), cytokines such as γ-interferon, IL-2, or IL-12 or genes encoding proteins involved in immune helper functions, such as B-7.

iii. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-α, MIP1-β, IP-10 and combinations thereof. The skilled artisan will recognize that certain cytokines (e.g., IFN's) are also known to have chemoattractant effects and could also be classified under the term chemokines.

iv. Immunogenic Carrier Proteins

The use of peptides for antibody generation or vaccination may requires conjugation of the peptide to an immunogenic carrier protein, such as hepatitis B surface antigen, keyhole limpet hemocyanin or bovine serum albumin. Means for conjugating a polypeptide or peptide to a immunogenic carrier protein are well known in the art and include, for example, glutaraldehyde, m-maleimidobenzoyl-N-hydroxysuccinimide ester, carbodiimide and bis-biazotized benzidine. Other immunopotentiating compounds are also contemplated for use with the compositions of the invention such as polysaccharides, including chitosan, which is described in U.S. Pat. No. 5,980,912, hereby incorporated by reference. Also, multiple (more than one) peptides may be crosslinked to one another (e.g., polymerized).

F. Combination Treatments

In certain embodiments, it may prove useful to use the vaccines of the present invention in conjunction with an antiviral therapy. The well known two classes of anti-virals are neuraminidase inhibitors and M2 inhibitors (adamantane derivatives). Neuraminidase inhibitors are currently preferred for flu virus infections. The CDC recommended against using M2 inhibitors during the 2005-06 influenza season.

Anti-viral drugs such as oseltamivir (Tamiflu®) and zanamivir (Relenza®) are neuraminidase inhibitors that are designed to halt the spread of the virus in the body. These drugs are often effective against both influenza A and B, and have been shown to be effective in combatting the recently emerged 2009 "swine" flu. The Cochrane Collaboration reviewed these drugs and concluded that they reduce symptoms and complications. Different strains of influenza viruses have differing degrees of resistance against these anti-virals, and it is impossible to predict what degree of resistance a future pandemic strain might have.

The anti-viral drugs amantadine and rimantadine are designed to block a viral ion channel (M2 protein) and prevent the virus from infecting cells. These drugs are sometimes effective against influenza A if given early in the infection but are always ineffective against influenza B. Measured resistance to amantadine and rimantadine in American isolates of H3N2 has increased to 91% in 2005. In contrast to neuraminidase inhibitors, amantadine and rimantadine have not proven effect again the 2009 "swine" flu.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Results

Using a bioinformatics approach, the inventor has identifed 35 peptides from influenza virus Matrix 1 protein, Matrix 2 protein and Nucleoprotein that bind HLA class I, and 16 peptides that bind HLA class II. These peptides were identified using a three-step selection process. First, "shared" epitopes were identified across the 1918 Spanish flu virus, standard vaccine strains, an H5 avian strain and the current H1N1 swine flu virus. Then, using T cell epitope prediction algorithms, these peptides were further culled. Finally, a set of peptides that were believed to be presented in common HLA haplotypes were identified, and sets of HLA class I and class II peptides were produced sufficient to ensure a 200% coverage of the population.

Figure 2:
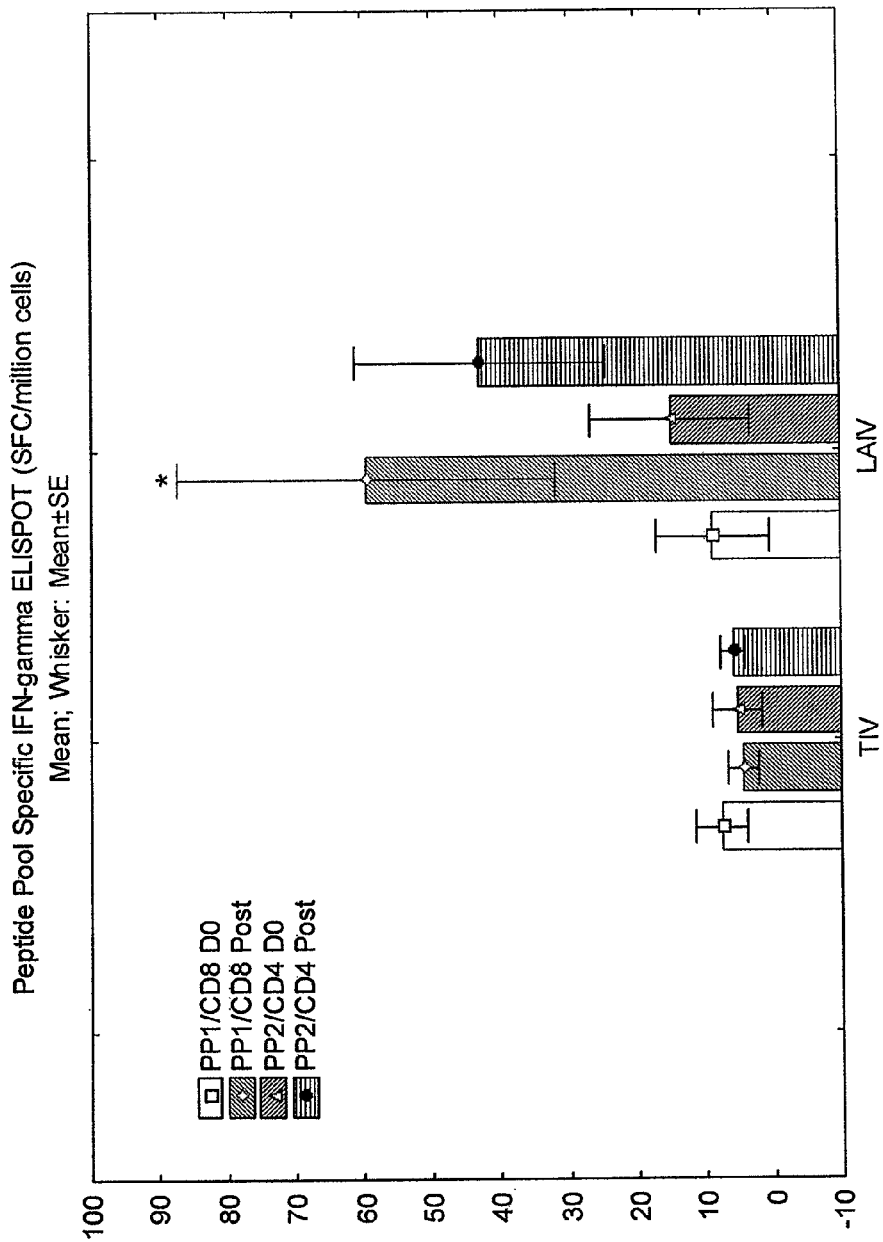
FIG. 2—ON Peptide Pool IFN-γ ELISPOT Assay. *, p<0.05 by Mann-Whitney U test (n=10/group).

These peptides were then screened for the ability to stimulate T cell response in peripheral blood samples from subjects in an NIH-sponsored, "Mix & Match" flu study (using both killed trivalent (TIV) and live attenuated (LAIV) vaccines) being conducted at the Saint Louis University VTEU. The results are shown in FIGS. 1-2. In summary, LAIV, but not TIV, induced infant flu-specific CD4+ T cells, LAIV, but not TIV, induced infant flu-specific CD8+ T cells, and LAIV, but not TIV, induced infant flu-specific δγ T cells. Moreover, LAIV, but not TIV, induced cell-mediated immunity against conserved epitopes.

Example 2

Future Studies

Study Subjects.

Peripheral blood samples will be collected from study subjects in the ongoing, NIH sponsored, "Mix & Match" flu study being conducted at the Saint Louis University VTEU. The inventor will be recruiting 60 children (15/group), aged 6-35 months to receive as follows:

Group A: 2 doses of TIV (trivalent inactivated vaccine)
Group B: 2 doses of LAIV (live attenuated infectious vaccine)
Group C: 1 dose of TIV followed by 1 dose of LAIV
Group D: 1 dose of LAIV followed by 1 dose of TIV All booster vaccinations will be given 30 days after the priming vaccinations. Blood samples will be collected at days 0, 30 and 60.

Antigens—live viruses. The following cold-adapted influenza vaccine strains will be obtained from MedImmune for in vitro stimulation assays:
1) A/New Caledonia/20/99
2) A/Wyoming/03/03
3) B/Jilin/20/2003

Antigens—Peptide Antigens.

Influenza peptide pools will be used in an in vitro assay to stimulate CD4$^+$ and CD8$^+$ T cell responses:
A. Focus on M1/M2 and NP proteins of influenza because they are about 90% conserved among subtypes of influenza.
B. Bioinformatics used to identify conserved sequences between NP/M1/M2 proteins expressed by the Influenza A vaccine strains and the potential H5N1 pandemic strains.
C. Predictive algorithms to identify MHC binding epitopes within the conserved regions of NP/M1/M2 proteins.
D. Conserved peptide sequences selected and included in 1 of 2 pools if they met the following criteria:
    1. If predicted to bind prevalent HLA types (i.e., HLA subtypes expressed in more than 10% of population; e.g., HLA-A2 & common DR types)
    2. Peptides with highest HLA binding scores
    3. If previously reported to be immunogenic
E. Two peptide pools prepared for in vitro stimulation assays:
    1. Peptide pool I to include 35 peptide sequences from M1, M2, and NP proteins of influenza predicted to bind prevalent HLA-class I molecules (Table 1)
    2. Peptide pool II to include 16 peptide sequences from M1, M2, and NP proteins of influenza predicted to bind prevalent HLA-class II molecules (Table 2)

In Vitro T Cell CFSE-Based Flow Cytometric Assay.

The inventor will study lymphocyte proliferation and IFN-γ production in the responding $CD4^+$, $CD8^+$ and γδ $TCR^+$ T cell subsets. CFSE-labeled peripheral blood lymphocytes harvested pre-vaccination, and on days 30 and 60 post-vaccination, will be cultured in the presence of live viruses, peptide pools and control antigens at pre-determined optimal doses and duration. After expansion, T cells will be harvested and stained for T cell surface markers and intracellular cytokines. Stained cells will then be analyzed by FACS to determine antigen specific $CD4^+$, $CD8^+$ and γδ $TCR^+$ T cells that have proliferated (dilute CFSE) and produced cytokines (e.g., IFN-γ).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference.

U.S. Pat. No. 4,435,386
U.S. Pat. No. 4,436,727
U.S. Pat. No. 4,436,728
U.S. Pat. No. 4,505,899
U.S. Pat. No. 4,505,900
U.S. Pat. No. 4,520,019
U.S. Pat. No. 4,554,101
U.S. Pat. No. 4,579,945
U.S. Pat. No. 4,866,034
U.S. Pat. No. 4,877,611
U.S. Pat. No. 4,950,645
U.S. Pat. No. 5,399,363
U.S. Pat. No. 5,466,468
U.S. Pat. No. 5,543,158
U.S. Pat. No. 5,641,515
U.S. Pat. No. 5,846,233
U.S. Pat. No. 5,980,912
Azuma et al., *Cell Immunol.*, 116(1):123-134, 1988.
Barany and Merrifield, In: *The Peptides*, Gross and Meienhofer (Eds.), Academic Press, NY, 1-284, 1979.
Benjamini et al., *Adv. Exp. Med. Biol.*, 303:71-77, 1991.
Capaldi et al., *Biochem. Biophys. Res. Comm.*, 74(2):425-433, 1977.
Houghten et al., *Infect. Immun.*, 48(3):735-740, 1985.
Husson et al., *J. Bacteriol.*, 172(2):519-524, 1990.
Jacobs et al., *Nature*, 327(6122):532-535, 1987.
Kobasa et al., *Nature*, 445(7125):319-23, 2007.
Kyte and Doolittle, *J. Mol. Biol.*, 57(1):105-32, 1982.
Lotte et al., *Adv. Tuberc. Res.*, 21:107-93; 194-245, 1984.
Luelmo, *Am. Rev. Respir. Dis.*, 125(3 Pt 2):70-72, 1982.
Martin et al., *Nature*, 345(6277):739-743, 1990.
Merrifield, *Science*, 232(4748):341-347, 1986.
Paul, *Transplant Proc.*, 25(2):2080-1, 1993.
PCT Appln. WO 91/16347
Rabinovich et al., *Science*, 265(5177):1401-1404, 1994.
Remington's Pharmaceutical Sciences, 15th ed., pages 1035-1038 and 1570-1580, Mack Publishing Company, Easton, Pa., 1980.
Stewart and Young, In: *Solid Phase Peptide Synthesis*, 2d. ed., Pierce Chemical Co., 1984.
Stites, *J. Mol. Biol.*, 235(1):27-32, 1994.
Takada et al., *J. Clin. Microbiol.*, 33(3):658-660, 1995.
Tam et al., *J. Am. Chem. Soc.*, 105:6442, 1983.
Yamamoto et al., *Jpn. J. Cancer Res.*, 79:866-873, 1988.
Yin et al., *J. Biol. Resp. Modif.*, 8:190-205, 1989.

What is claimed is:

1. A method of inducing an anti-influenza immune response in a subject comprising administering to a subject a first influenza peptide and a second influenza peptide each being 9-15 residues in length, wherein said first and second peptides are SEQ ID NO: 3 and 43.

2. The method of claim 1, wherein at least one of said peptides is/are fused to another amino acid sequence.

3. The method of claim 1, wherein at least 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, or 49 additional peptides selected from SEQ ID NOS: 1, 2, 4-42 and 44-51 are administered to said subject.

4. The method of claim 1, wherein administration comprises injection.

5. The method of claim 4, wherein in injection comprises subcutaneous or intramuscular injection.

6. The method of claim 1, wherein administration comprises inhalation.

7. The method of claim 6, wherein inhalation comprises inhaling a nasal aerosol or mist.

8. The method of claim 1, wherein said peptides are administered with an adjuvant.

9. The method of claim 8, wherein said adjuvant is a squalene adjuvant, a cytokine adjuvant, a lipid adjuvant or a TLR ligand.

10. The method of claim 1, wherein the total amount of peptide administered is between 50 µg/kg and 1 mg/kg.

11. The method of claim 1, wherein at least one of said peptides is administered at least a second time.

12. The method of claim 1, further comprising a second administration to said subject of at least one peptide distinct from the peptides of the initial administration.

13. The method of claim 1, further comprising administration of a live-attenuated vaccine or a killed vaccine to said subject.

14. The method of claim 1, wherein said subject is a human subject.

15. The method of claim 1, further comprising measuring a $CD4^+$, a $CD8^+$ and/or a $\gamma\delta$ T cell response in said subject following administration.

* * * * *